United States Patent [19]

Pesnelle et al.

[11] 4,064,181
[45] Dec. 20, 1977

[54] PREPARATION OF NOVEL ETHERS

[75] Inventors: Pierre Pesnelle, Rueil-Malmaison; Paul José Teisseire, Grasse, both of France

[73] Assignee: Societe Anonyme Roure Bertrand Dupont, Paris, France

[21] Appl. No.: 723,719

[22] Filed: Sept. 16, 1976

Related U.S. Application Data

[62] Division of Ser. No. 444,488, Feb. 21, 1974.

[30] Foreign Application Priority Data

Feb. 28, 1973 Switzerland .................... 2885/73

[51] Int. Cl.² .................... C07C 43/20; C07C 43/00
[52] U.S. Cl. .................... 260/611 F; 260/611 A;
260/395; 260/598; 260/617 F; 260/586 F;
252/522; 560/117
[58] Field of Search ............ 260/586 F, 590 F, 617 F,
260/611 A, 611 F

[56] References Cited

U.S. PATENT DOCUMENTS 3,879,466  4/1975  Light ............................. 260/617 F
3,925,486  12/1975  Grewter et al. ................ 260/611 F
4,000,202  12/1976  Maupetit et al. ............... 260/586 F

OTHER PUBLICATIONS

Mirrington et al., J. Org. Chem., vol. 37, pp. 2871-2881 (1972).

Primary Examiner—James O. Thomas, Jr.
Assistant Examiner—James H. Reamer
Attorney, Agent, or Firm—Wallenstein, Spangenberg, Hattis & Strampel

[57] ABSTRACT

Novel ethers which are represented by the general formula

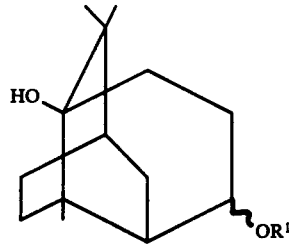

. XI wherein $R^1$ represents methyl or benzyl, and process for the preparation of said ethers.

1 Claim, No Drawings

PREPARATION OF NOVEL ETHERS

This application is a division of application Ser. No. 444,488, filed Feb. 21, 1974.

This invention relates to novel ethers which are represented by the general formula

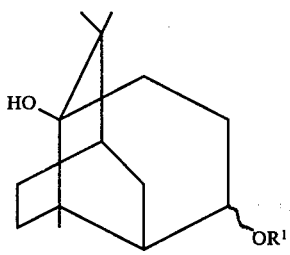

XI wherein $R^1$ represents methyl or benzyl.

The novel ethers of the present invention have been found to have especial utility as intermediates for the production of norpatchoulenol (sometimes denoted as nordehydropatchoulol) which is an unsaturated tricyclic alcohol having the formula

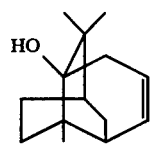

and which is an odorant material which is highly useful for imparting odors akin to Patchouli Oil to various products.

The novel ethers of the present invention can be prepared by a process utilizing, as an intermediate, a compound corresponding to the following formula

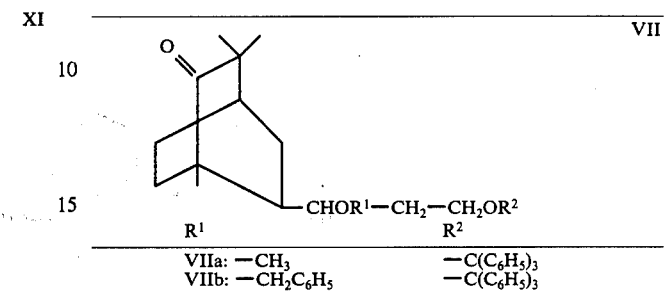

VII

| $R^1$ | $R^2$ |
|---|---|
| VIIa: —CH$_3$ | —C(C$_6$H$_5$)$_3$ |
| VIIb: —CH$_2$C$_6$H$_5$ | —C(C$_6$H$_5$)$_3$ | and converting it in the manner hereafter described to the aforesaid novel ethers of the present invention. The prepararion of said intermediate compound VII is also shown below starting with the unsaturated bicyclic aldehyde represented by formula I below. The overall reaction scheme is as follows:

Reaction scheme

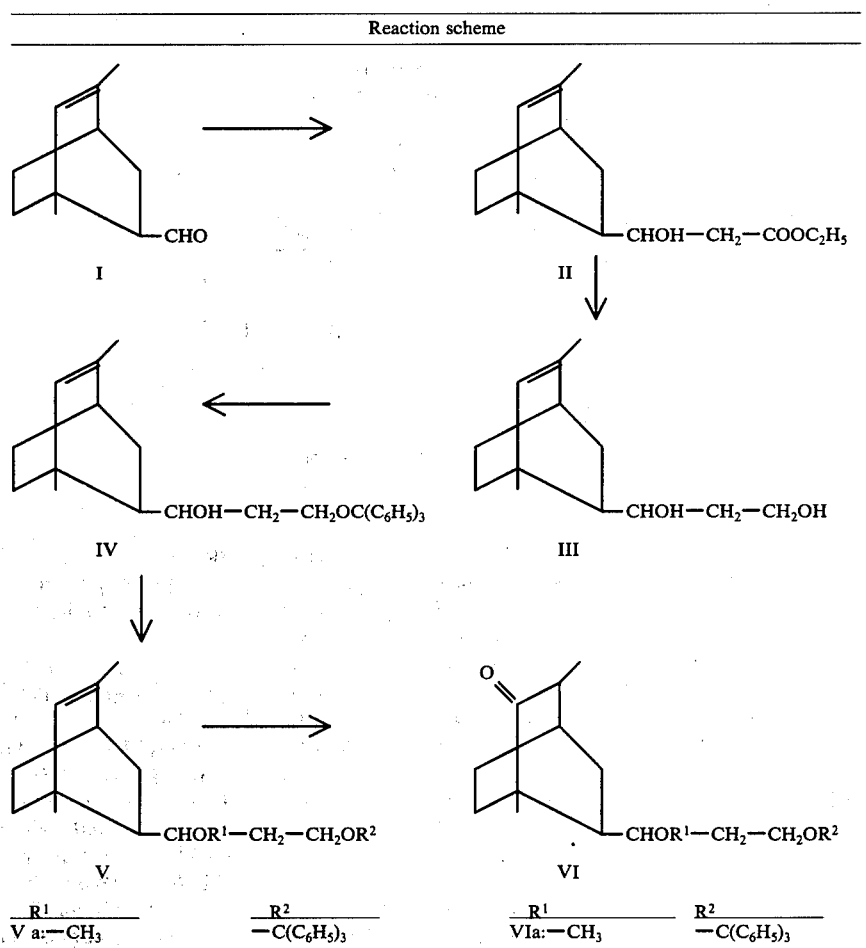

| | $R^1$ | $R^2$ |
|---|---|---|
| V a: | —CH$_3$ | —C(C$_6$H$_5$)$_3$ |
| VIa: | —CH$_3$ | —C(C$_6$H$_5$)$_3$ |

-continued
Reaction scheme

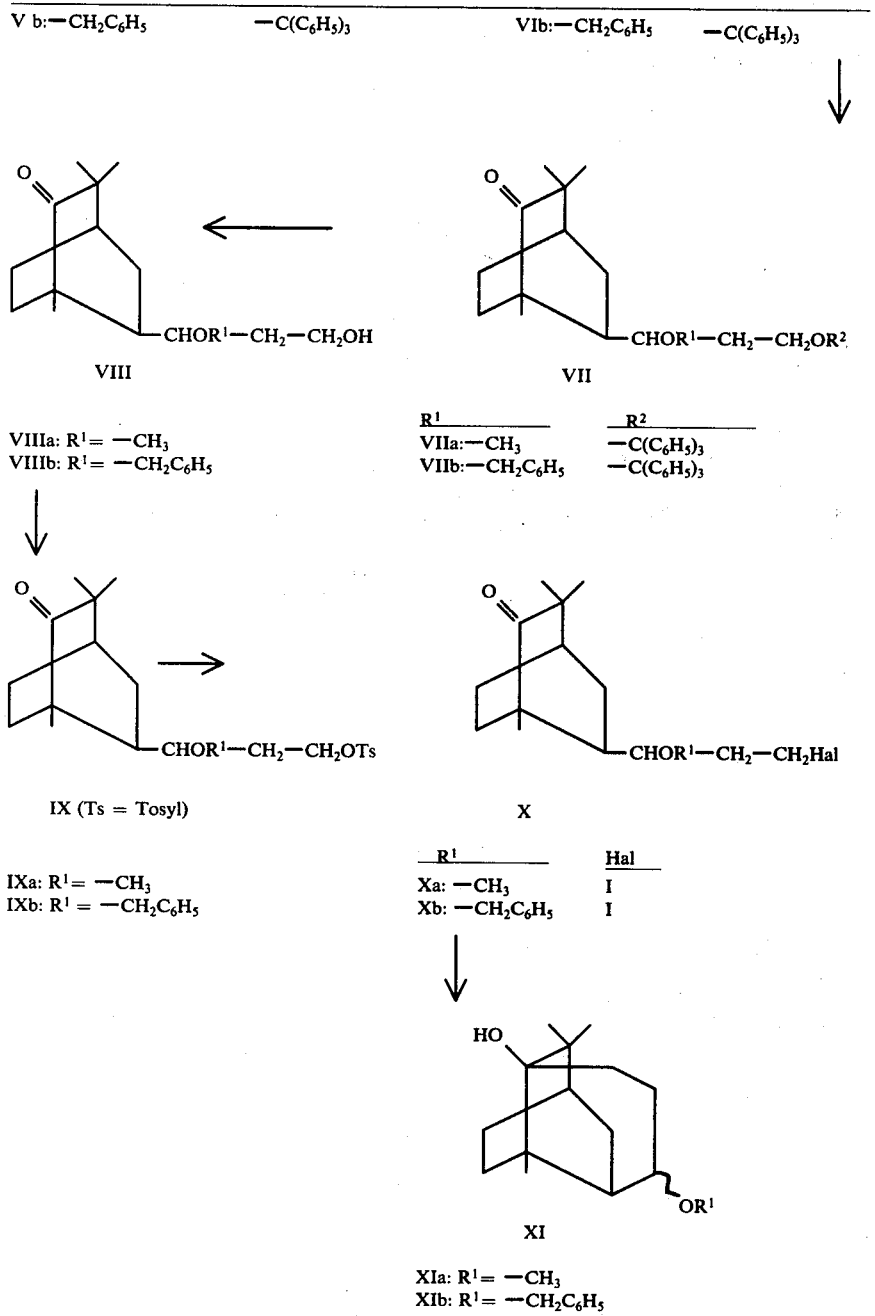

The synthesis takes as its starting point the unsaturated bicyclic aldehyde I, which can be obtained according to J.Org.Chem. 37 (1972), 2871. Treatment of this aldehyde I with ethyl bromacetate in the presence of zinc according to the Reformatsky reaction yields the ester II (as a diastereomeric mixture), whose ester group can be reduced to a primary alcohol group by means of LiAlH$_4$. By recrystallization from petroleum ether, there can be obtained from the so obtained mixture of the two diastereomeric glycols III, one of which is in the crystalline form m.p. 113°–114° C. The reactions described below are based on this isomer.

First, the primary OH group of the alcohol III is etherified using a triphenylhalomethane, preferably triphenylchloromethane. The secondary OH group of the so obtained trityl ether IV is then etherified. By methylation, there is thus obtained the methyl trityl ether V a and, by benzylation, the benzyl trityl ether V b.

By hydroboronation and oxidation, the compounds of the formula V can be converted into the corresponding ketones of the formula VI and the latter can be converted by methylation into the compounds of the formula VII. From these, there are obtained, after hydrogenolysis or hydrolytic cleavage of the trityl group, the free primary alcohols of the formula VIII. Via the tosylate of the formula IX, there are then attained the halides X (wherein "Hal" may be iodine, chlorine or bromine) which, after cycliastion, finally yield the tricyclic monoethers of the formula XI.

The invention will now be illustrated with reference to the following Examples.

EXAMPLE 1 a. To a 100 ml flask there are added 3.3 g (15 mmol) of the diol III, 6 g of trityl chloride (21 mmol), 50 ml of anhydrous benzene and 3 ml of pyridine. The mixture is held for 2 hours under reflux. After cooling, the precipitated pyridine chloride is filtered off, the solvent distilled off and the residue taken up in a petroleum ether/ether mixture (8:2). After filtration over 100 g of neutral $Al_2O_3$ of activity 1, there are obtained 4 g of the trityl monoether IV IR: 3500, 3090, 3060, 1600, 1490, 1070, 705 and 760 $cm^{-1}$

NMR 1.10, 1.70, ~3-4, 5.36.

b. To a flask provided with a stirrer, there are added 5.9 g (13 mmol) of trityl monoether IV, 60 ml of glyme, 2 g (14 mmol) of methyl iodide and then 0.8 g of sodium hydride (50%, 15 mmol) are added in small portions. The mixture is then heated over 2 hours to reflux, there are successively added a further 2 g of methyl iodide and 0.5 g of sodium hydride, whereupon the reaction is terminated after a further 2 hours. The reaction mixture is mixed with 100 ml of ether and then with 5 ml of water. The ethereal solution is then washed with saturated NaCl solution until neutral. The solution is dried over sodium sulphate and the solvent distilled off. There are thus obtained 7.4 g of crude diether V a, which is purified by chromatography over 100 g of neutral aluminium oxide. The yield of thin-layer chromatographically homogeneous diether V a amounts to 6.65 g.

IR: 3030, 3060, 3020, 2820, 1600, 1495, 1070, 1095 700, 745, 1650 $cm^{-1}$

NMR: 1.14, 1.72, 3.01, 5.42 ~ 7.20 c. 1 g of the diether V a, dissolved in 15 ml of tetrahydrofuran, is treated at 0° C with a stream of diborane ($B_2H_6$). The reaction is followed by thin-layer chromatography. After disappearance of the starting material, several drops of water are added and the mixture is then poured into 20ml of water. The mixture is then extracted with 4 times 10 ml of benzene, washed with 2 times 10 ml of saturated NaCl solution, dried over sodium sulphate and the solvent distilled off. There are obtained 1.1 g of crude borane. For the oxidation of the obtained borane, this crude porane is dissolved in 15 ml of pyridine and the solution added to a solution of 1.6 g of $CrO_3$ in 16 ml of pyridine. The mixture is stirred overnight at room temperature, poured into 60 ml of ether and the precipitate filtered off and washed with ether. The organic phase is washed with 10% cold hydrochloric acid until neutral. After drying and distillation off of the ether, there are obtained 1.1 g of crude ketone VI a. After chromatography over 25 g of neutral aluminium oxide (elution with petroleum ether/ether 8*2), 200 mg of ketone VI a are obtained with the following spectral data:

IR: 3080, 3060, 3020, 2820, 1710, 1595, 1490, 1080, 705, 750, 760 $cm^{-1}$ d. Manufacture of trityl potassium: 100 mg of potassium cut up into fine segments are added to a solution of 600 mg ph triphenylmethane in 5 ml of glyme. The mixture is stirred at room temperature under an inert atmosphere for 16 hours.

Alkylation: To a 25 ml flask provided with a stirred there is added a solution of 200 mg of the ketone VI a in 5 ml of glyme and a sufficient amount of trityl potassium. If the red colouration remains, the mixture is stirred for 20 minutes and then mixed with 0.5 ml of methyl iodide. After 6 hours at room temperature, the reaction mixture is poured into 25 ml of water and then extracted with 3 times 20 ml of ether. The extracts are washed with water and then with saturated NaCl solution. After drying over sodium sulphate, the solvent is evaporated. After chromatography of the crude product through 50 g of neutral aluminium oxide, there are obtained 25 mg of methylated ketone VII a as well as 100 mg of the starting material.

IR: 3080, 3060, 3020, 1710, 1595, 1485, 1075, 1060, 2820, 770, 760, 750, 1380, 1375, cm $^{-1}$

NMR: 0.95, 1.04, 1.08, 3.08, 3.36, 7.26 e. A solution of 1.45 g of crude ketone VII a in 100 ml of ethanol is treated with hydrogen in the presence of 0.25 g of palladium on carbon (5%). The hydrogenolysis is continued for 17 hours. After filtration of the catalyst, the solvent is distilled and the residue chromatographed through a column of 40 g of silica gel. Elution with a petroleum ether/ether mixture (3:7) produces 125 mg of the alcohol VIII a.

IR: 3320, 2830, 1705, 1085 $cm^{-1}$

NMR: 0.86, 1.08, 3.32 f. 101 mg of the alcohol VIII a are dissolved in 9 ml of pyridine. The mixture is cooled to −12° C and 300 mg of tosyl chloride added. The mixture is left to stand for 14 hours at ca. −14° C; then the reaction mixture is poured into 50 ml of 10% hydrochloric acid and extracted with ether (3 times 20 ml). The organic phase is washed with 10% hydrochloric acid and then with aqueous sodium bicarbonate solution. The obtained tosylate IX a (100 mg) does not need to be purified for the subsequent reaction.

g. 100 mg of the so obtained tosylate IX a, dissolved in 15 ml of acetone, are treated for 20 hours at room temperature with 300 mg of NaI. The reaction mixture is poured into 30 ml of water and then extracted with 3 times 15 ml of ether. After washing with water and drying over sodium sulphate, the solvent is evaporated off. There are obtained 87 mg of crude iodide X a, which is chromatographed through 6 g of neutral aluminium oxide. Elution with a petroleum ether/ether mixture 8:2 produces 68 mg of iodide X a.

h. To a 10 ml flask there are added 68 mg of iodide X a, dissolved in 5 ml of tetrahydroduran, and then 100 mg of finely divided sodium. the misture is stirred for 4 hours under reflux, then cooled to room temperature, the solvent removed and the sodium washed with tetrahydrofuran. There is added 1 ml of water and the mixture is acidified with 10% hydrochloric acid. After the addition of 25 ml of ether, the mixture is decanted, washed with bicarbonate solution and dried over sodium sulphate. After evaporation of the solvent, there are obtained 44 mg of crude cyclisation product XI a. Chromatography through a column of 5 g of silica gel and elution with a petroleum ether/ether mixture 8:2 yield 17 mg of cyclisation product XI a.

IR: 3460, 2820, 1085 $cm^{-1}$

MNR* 0.78, 1.02, 1.07, 3.18

Mass spectrum: 238, 220, 206, 195, 191, 188, 177', 163, 145, 109, 93, 81, 69, 55.

EXAMPLE 2

By analogy with the process of Example 1b there is obtained from the trityl monoether IV by reaction with benzyl chloride (c.f. Canad. J. of Chem. 44 (1966), 1591) the diether V b with the following spectral data:
IR: 3060, 3020, 1600, 1490, 1090, 1070, 700, 745 cm⁻¹

NMR: 1.11, 1.72 ~2.13 ~2.75 4.28 5.42

The oxidation of the obtained diether V b according to Example 1c leads to the ketone VI b, which can be methylated to the compound VII b by analogy with the process of Example 1 d. After selective cleavage of the trityl group, with acetic acid in homogeneous ethereal phase at room temperature (c.f. e.g. J. Chem. Soc. 1956, 3459), the obtained monether VIII b is converted into the tosylate IX b (by analogy with the process of Example 1 f); this is converted into the iodide X b (according to the process of Example 1 g), whereupon finally the cyclisation (according to Example 1 h) leads to the tricyclic benzyl ether XI b.

As ointed out above, the novel ethers of the present invention, represented by formula XI, are especially useful in the production of norpatchoulenol. To this end, for instance, the tricyclic benzyl ether of formula XI b is first converted by ether cleavage, especially by hydrogenolysis, to the free diol of formula XII

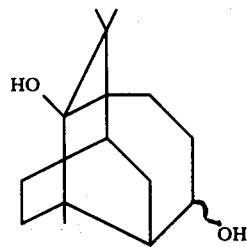

XII the benzyl group being readily cleavable in accordance with conventional methods of hydrogenolytic benzyl ether cleavage. Then, the dehydration of the diol XII to norpatchoulenol XIII

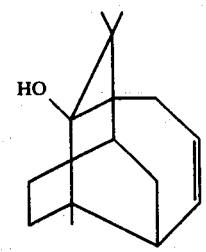

XIII can be carried out as described below with reference to a diol XIII having the S configuration of the carbon carrying the secondary OH group:

400 mg of the above mentioned diol in 1 ml of pyridine are mixed with a solution of 500 mg (2.06 mmol) of p-bromo-benzenesulphonyl chloride in 1 ml of pyridine. The mixture is stirred for 1.5 hours at 0° C, then poured onto ice and extracted with ether. After extraction, washing to neutrality, drying and distillation of the ether, there are obtained 300 mg of a light yellowish crystallized product, which is chromatographed through a column of 10 g of silica gel. Elution with a petroleum ether/ether mixture (9:1) yields firstly 100 mg of a crystalline mixture of 2 products, with norpatchoulenol XIII as the main product. Further elution with petroleum ether/ether mixture 7:3 yields 160 mg of unreacted diol XII. Melting point of the thus obtained pure norpatchoulenol: 180°—183° C.

What is claimed is:
1. Compounds of the formula

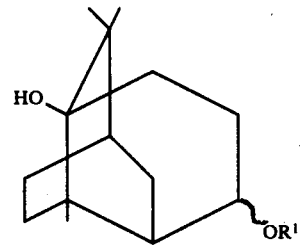

XI wherein R¹ represents methyl or benzyl.

* * * * *